(12) United States Patent
Munro

(10) Patent No.: US 6,551,988 B1
(45) Date of Patent: Apr. 22, 2003

(54) FRAGRANCE COMPOUNDS

(75) Inventor: David Munro, Kent (GB)

(73) Assignee: Quest International B.V., Naarden (NL)

( * ) Notice: Subject to any disclaimer, the term of this patent is extended or adjusted under 35 U.S.C. 154(b) by 0 days.

(21) Appl. No.: 09/719,774

(22) PCT Filed: Jun. 15, 1999

(86) PCT No.: PCT/GB99/01905

§ 371 (c)(1),
(2), (4) Date: Dec. 18, 2000

(87) PCT Pub. No.: WO99/65852

PCT Pub. Date: Dec. 23, 1999

(30) Foreign Application Priority Data

Jun. 18, 1998 (EP) .............................. 98304816

(51) Int. Cl.$^7$ ........................... A61K 7/46; C07C 49/547
(52) U.S. Cl. ................. 512/8; 512/25; 512/26; 512/27; 568/303; 568/338; 568/342; 568/375
(58) Field of Search ................. 512/8, 25, 26, 512/27; 568/303, 338, 342, 375

(56) References Cited

U.S. PATENT DOCUMENTS 4,393,245 A * 7/1983 Hoffman et al. ............ 568/375

FOREIGN PATENT DOCUMENTS

| EP | 0 033 763 | 8/1981 |
| FR | 1.579.952 | 8/1969 |

OTHER PUBLICATIONS

Zakharkin L I et al: "Simple synthesis of acetyl–and propionylcyclododecanes" Russian Chemical Bulletin, vol. 42, No. 2, 1993, pp. 382–383, XP002085020 Russ. Acad. Sci.; A. N. Nesmeyanov Inst. Organoelement Compd.; Moscow; 117813; Russia (RU) the whole document.

* cited by examiner

*Primary Examiner*—Jill Warden
*Assistant Examiner*—Monique T. Cole
(74) *Attorney, Agent, or Firm*—Morgan, Lewis & Bockius LLP

(57) ABSTRACT

4,8-cyclododecadienyl ketones having formula (I), in which R has up to 5 carbon atoms, are novel compounds exhibiting woody/amber odor characteristics which find use in perfumes and in perfumed products.

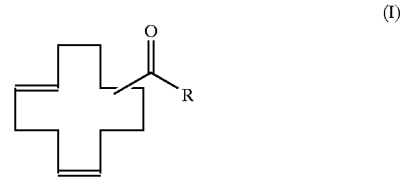

10 Claims, 2 Drawing Sheets

QRM 2815

Reagents: (i) m-CPBA, CH$_2$Cl$_2$  (ii) MgI$_2$, Et$_2$O  (iii) TMSC(Li)N$_2$

FRAGRANCE COMPOUNDS

FIELD OF THE INVENTION

This invention concerns novel fragrance compounds, their method of production and use in perfumes and perfumed products.

SUMMARY OF THE INVENTION

In one aspect the invention provides 4,8-cyclododecadienyl ketones. These constitute a group of novel ketones, based on a 12 membered ring having two positions of unsaturation, having the general structure shown below, in which side chain R is an alkyl group which may have up to 5 carbon atoms.

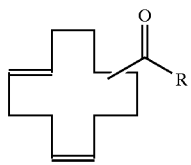

(I)

For brevity and simplicity, such materials will be referred to herein as "the ketones", "the novel ketones" or "the ketones of the invention". The general structure given above indicates that different isomers or a mixture of isomers are included in the term "the ketones", as discussed in more detail hereinafter. In particular, the preferred compounds of the invention comprise a mixture of the isomers illustrated in FIG. 3.

The ketones of the invention exhibit woody/amber/musky odour characteristics, and so may be used as such to impart, strengthen or improve the odour of a wide variety of products, or may be used as a component of a perfume (or fragrance composition) to contribute its odour character to the overall odour of such perfume. For the purposes of this invention a perfume is intended to mean a mixture of fragrance materials, if desired mixed with or dissolved in a suitable solvent or mixed with a solid substrate, which is used to impart a desired odour to the skin and/or any product for which an agreeable odour is indispensable or desirable. Examples of such products are: fabric washing powders, washing liquids, fabric softeners and other fabric care products; detergents and household cleaning, scouring and disinfection products; air fresheners, room sprays and pomanders; soaps, bath and shower gels, shampoos, hair conditioners and other personal cleansing products; cosmetics such as creams, ointments, toilet waters, preshave, aftershave, skin and other lotions, talcum powders. body deodorants and antiperspirants, etc.

Other fragrance materials which can be advantageously combined with a ketone according to the invention in a perfume are, for example, natural products such as extracts, essential oils, absolutes, resinoids, resins, concretes etc., but also synthetic materials such as hydrocarbons, alcohols, aldehydes, ketones, ethers, acids, esters, acetals, ketals, nitriles, etc., including saturated and unsaturated compounds, aliphatic, carbocyclic and heterocyclic compounds.

Such fragrance materials are mentioned, for example, in S. Arctander, Perfume and Flavor Chemicals (Montclair, N.J., 1969), in S. Arctander, Perfume and Flavor Materials of Natural Origin (Elizabeth, N.J., 1960) and in "Flavor and Fragrance Materials—1991", Allured Publishing Co. Wheaton, Ill. USA.

Examples of fragrance materials which can be used in combination with a ketone according to the invention are: geraniol, geranyl acetate, linalol, linalyl acetate, tetrahydrolinalol, citronellol, citronellyl acetate, dihydromyrcenol, dihydromyrcenyl acetate, tetrahydromyrcenol, terpineol, terpinyl acetate, nopol, nopyl acetate, 2-phenyl-ethanol, 2-phenylethyl acetate, benzyl alcohol, benzyl acetate, benzyl salicylate, styrallyl acetate, benzyl benzoate, amyl salicylate, dimethylbenzyl carbinol, trichloromethylphenylcarbinyl acetate, p-tert-butylcyclohexyl acetate, isononyl acetate, vetiveryl acetate, vetiverol, α-hexylcinnamaldehyde, 2-methyl-3-(p-tert-butylphenyl)propanal, 2-methyl-3-(p-iso-propylphenyl) propanal, 3-(p-tert-butylphenyl)propanal, 2,4-dimethylcyclohex-3-enyl-carboxaldehyde, tricyclodecenyl acetate, tricyclodecenyl propionate, 4-(4-hydroxy-4-methylpentyl)-3-cyclohexenecarboxaldehyde, 4-(4-methyl-3-pent-enyl)-3-cyclohexenecarboxaldehyde, 4-acetoxy-3-pentyl-tetrahydropyran, 3-carboxymethyl-2pentylcyclopentane, 2-n-heptylcyclopentanone, 3-methyl-2-pentyl-2-cyclopentenone, n-decanal, n-dodecanal, 9-decenol-1, phenoxyethyl isobutyrate, phenylacetaldehyde dimethylacetal, phenylacetaldehyde diethylacetal, geranyl nitrile, citronellyl nitrile, cedryl acetate, 3-isocamphylcyclohexanol, cedryl methyl ether, isolongifolanone, aubepine nitrile, aubepine, heliotropin, coumarin, eugenol, vanillin, diphenyl oxide, hydroxycitronellal, ionones, methylionones, isomethylionones, irones, cis-3-hexenol and esters thereof, indan musks, tetralin musks, isochroman musks, macrocyclic ketones, macrolactone musks, ethylene brassylate.

Solvents which can be used for perfumes which contain the ketones according to the invention are, for example: ethanol, isopropanol, diethyleneglycol monoethyl ether, dipropylene glycol, diethyl phthalate, triethyl citrate, isopropyl myristate, etc.

The quantities in which a ketone according to the invention can be used in perfumes or in products to be perfumed may vary within wide limits and depend, inter alia, on the nature of the product, on the nature and the quantity of the other components of the perfume in which the ketone is used and on the olfactive effect desired. It is therefore only possible to specify wide limits, which, however, provide sufficient information for the specialist in the art to be able to use the ketone according to the invention for his specific purpose. In perfumes an amount of 0.01% by weight or more of a ketone according to the invention will generally have a clearly perceptible olfactive effect. Preferably the amount is 0.1–80% by weight, more preferably at least 1%. The amount of the ketone according to the invention present in products will generally be at least 10 ppm by weight, preferably at least 100 ppm, more preferably at least 1000 ppm. However, levels of up to about 20% by weight may be used in particular cases, depending on the product to be perfumed.

In a further aspect the invention thus provides a perfume comprising a ketone of the invention in an olfactively effective amount.

The invention also covers a perfumed product comprising a ketone of the invention.

The ketones of the invention may be produced from the aldehyde 4,8-cyclododecadiene-1-carbaldehyde (referred to herein as QRM 2815) by reaction with a range of Grignard reagents (RMgX), followed by chromic acid oxidation, as illustrated in FIG. 1. A range of ketones in accordance with the invention have been produced in this way, with side chains R and odour properties as follows:

| R | QRM number | Odour Description | Chemical Name |
|---|---|---|---|
| Methyl | 2828 | Not screened | 1-(4,8-cyclododecadienyl)-1-ethanone |
| Ethyl | 2843 | Cedarwood, amber, pepper | 1-(4,8-cyclododecadienyl)-1-propanone |
| n-propyl | 3101 | Woody, musk | 1-(4,8-cyclododecadienyl)-1-butanone |
| iso-propyl | 2885 | Woody, amber | 1-(4,8-cyclododecadienyl)-2-methyl-1-propanone |
| n-butyl | 3102 | Not screened | 1-(4,8-cyclododecadienyl)-1-pentanone |
| sec-butyl | 3056 | Amber/woody, fruity | 1-(4,8-cyclododecadienyl)-2-methyl-1-butanone |
| 2-propenyl | 2924 | Amber/woody, chypre | 1-(4,8-cyclododecadienyl)-2-buten-1-one |

The side chain R may thus be a straight chain or branched, saturated or unsaturated. R has up to 5 carbon atoms, resulting in a molecule having at least 18 carbon atoms. Molecules with more than 18 carbon atoms tend to have a vapour pressure that is too low for the molecule to have odour value.

Isopropylmagnesium chloride is conveniently used as the Grignard reagent to produce the ketone QRM 2885 in this way, with other Grignard reagents (RMgX) being used as appropriate in analogous manner to produce other ketones.

The ketones can exist in different isomeric forms, and the invention covers each isomeric form alone, and mixtures of different isomeric forms. The preparative technique used has a major influence on the relative proportions of the different isomeric forms.

The aldehyde QRM 2815 may be produced from 1,5,9-cyclododecatriene, which is a cheap and readily accessible starting material, by the reaction shown in FIG. 2, in which the cyclododecatriene is converted to cyclododecatriene monoepoxide by reaction with a peroxy acid followed by catalysed isomerisation. The reaction is described in more detail below.

An alternative preparative route to the aldehyde comprises hydrofomylation of 1,5,9-cyclododecatriene by reaction with hydrogen and carbon monoxide in the presence of a catalyst such as a rhodium catalyst.

Of the ketones of the invention produced and tested so far, QRM 2885 (R=iso-propyl) is currently favoured as a fragrance material as it has good odour characteristics and a good balance of initial impact and substantivity properties. The compound is also predicted to be biodegradable, but this has not yet been tested.

QRM 2885 occurs as two geometrical isomers. When the aldehyde QRM 2815 is prepared by the route shown in FIG. 2, QRM 2885 is produced as an isomeric mixture of (Z,E)-4,8-cyclododecadienyl-2-methyl-1-propanone [isomer A] (89%), and (E,Z)-4,8-cyclododecadienyl-2-methyl-1-propanone [isomer B] (7%), as shown in FIG. 3. However, when the aldehyde is prepared by the hydroformylation route described above, the two isomers were found to be present in approximately equal amounts. The two isomers are preferably present in a ratio of A:B in the range 95:5 to 5:95 by weight, more preferably in the range 90:5 to 40:60, A:B by weight and, most preferably, in the range 55:45 to 45:55, A:B by weight. Each of the geometric isomers of QRM 2885 exists as two optical isomers and the ketones of the invention include mixtures of optical isomers.

Glc olfactometry indicated both isomers to have a woody amber odour, with the (Z,E)-4,8-cyclododecadienyl-2-methyl-1-propanone isomer appearing to have a drier odour quality. Excellent performance on both wet and dry cloth, from fabric conditioner, was exhibited by QRM 2885 against the standards of the known fragrance materials Cyclisone (Cyclisone is a Trade Mark) from Quest International and Iso E Super (Iso E Super is a Trade Mark) from Acedsa.

The ketone QRM 2885 is useful as a fragrance material both as an isomeric mixture as prepared, and as individual isomers.

The invention will be further described, by way of illustration, in the following Examples and with reference to the accompanying figures in which.

EXAMPLE 1

Synthesis of 1-(4.8-cyclododecadienyl)-2-methyl-1-propanone (ORM 2885)

a) Synthesis of 4,8-Cyclododecadiene-1-carbaldehyde (QRM 2815)

Figure 2:
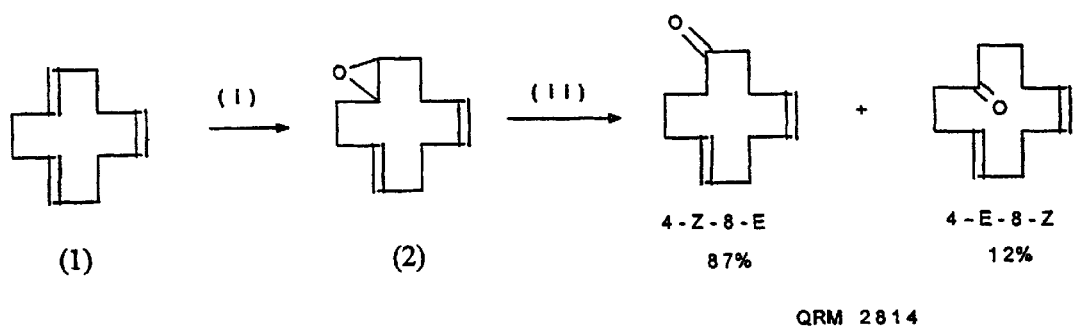
FIG. 2 shows a reaction scheme for production of 4,8-cyclododecadiene-1-carbaldehyde.
Figure 2:
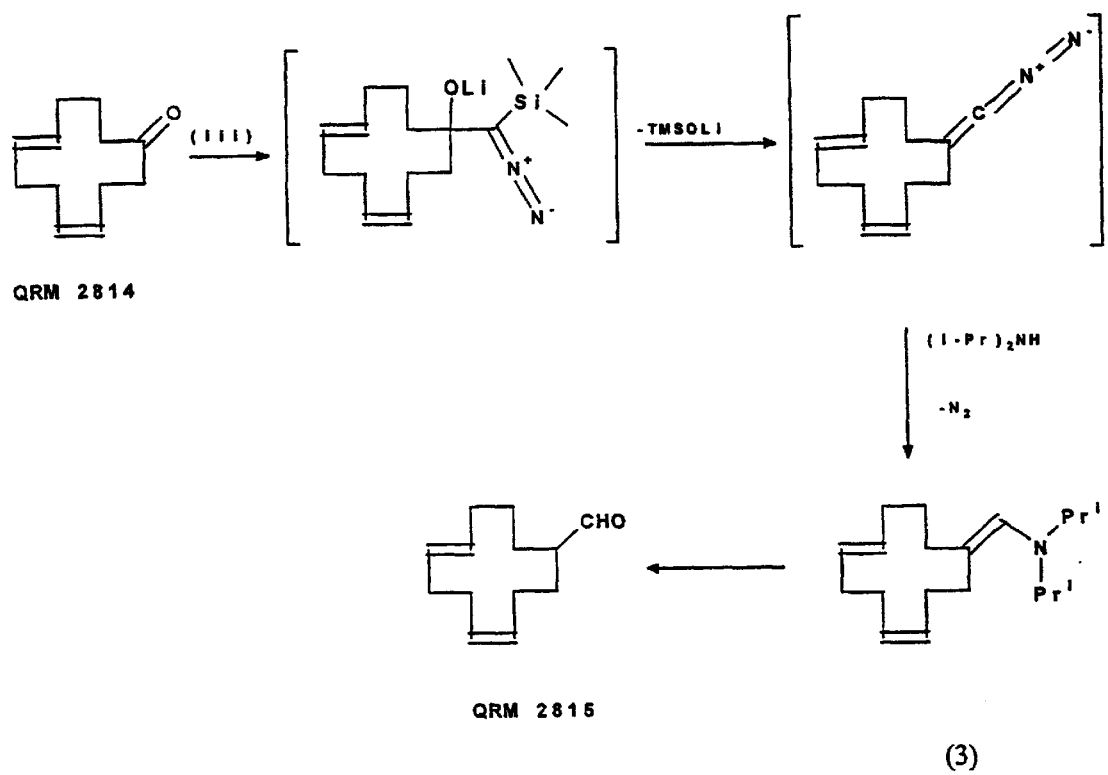

4,8-cyclododecadiene carboxaldehyde (QRM 2815) was produced from 1,5,9-cyclododecatriene by the reaction illustrated in FIG. 2.

1,5,9-cyclododecatriene ((1) in FIG. 2) was reacted with one equivalent of metachloroperoxybenzoic acid (m-CPBA) in the presence of $CH_2Cl_2$ to give 1,5,9-cyclododecatriene monoepoxide ((2) in FIG. 2). This is consistent with the reported relative susceptibility of the E-bonds to electrophilic reagents (H. Nozaki. S. Kato, R. Noyoru, Can. J. Chem., 44, 1021, (1966)).

Isomerisation of this epoxide by a $MgI_2$-catalysed rearrangement in the presence of diethyl ether (German Patent No. 1 075 601) gave cyclododecadienone (referred to herein as QRM 2814) as a mixture of isomers, 4-Z-8-E-(87%) and 4-E-8-Z-(12%) (F. Lombardo, R. A. Newmark, E. Kariv-Miller J.Org.Chem. 56, 2422, (1991)). In order to retain this known isomer ratio, homologation of the ketone QRM 2814 to 4,8-cyclododecadienylcarboxaldehyde (QRM 2815) was therefore carried out by reaction with lithium trimethylsilyldiazomethane (K. Miwa, T. Aoyama, T. Shiori Synlett, 109, (1994)), in the presence of excess diisopropylamine, to give the enamine ((3) in FIG. 2), which was readily hydrolysed to the aldehyde, QRM 2815, merely by stirring over wet silica.

Considering matters in more detail, 1,5,9-cyclododecatriene monoepoxide [100 g; 0.56 mol] was dissolved in $Et_2O$ (300 ml), and magnesium iodide [10 g; 0.036 mol] added. The mixture was placed in a 1 litre Buchi autoclave, and heated at 70° C., with stirring, monitoring reaction progress by glc [SE 54; 100–250° at 4° C./min]

| Epoxide | Reaction mixture |
| --- | --- |
| 16.408 min (94%) | 15.753 min (12%) |
| | 15.858 min (87%) |

After cooling, the reaction mixture was partitioned ($Et_2O$/$H_2O$), and the organic layer was separated, washed, dried, and flash chromatographed [silica:hexane 90%, $Et_2O$ 10%] to give a colourless oil (89.2 g, 89%), which was used directly in the next stage.

i-$Pr_2NH$ [80 g; 0.79 mol] was added to tetrahydrofuran (THF) (100 ml), cooled to −30° C., and n-BuLi [40 ml of 2.5 M, 0.1 mol] added dropwise by syringe, under $N_2$. (Trimethylsilyl)diazomethane ($TMSCHN_2$) [50 ml; 1.9 M in hexane; 0.095 mol] was added dropwise to this lithium diisopropylamide (LDA) solution at −70° C. After complete addition, a solution of 4,8-cyclododecadien-1-one [14.2 g; 0.08 mol] in anhydrous THF (50 ml) was added, and the reaction mixture allowed to stir for 1 hour at −70° C., then allowed to reach ambient temperature. It was, subsequently, refluxed for 3 hours. Most of the THF was removed in vacuo, $Et_2O$ (300 ml) was added, and the reaction mixture poured into ice-water. After extraction into $Et_2O$, the solvent was removed, the residue redissolved in ethyl acetate (300 ml), and silica gel (100 g) added, together with $H_2O$ (1 ml). The mixture was stirred overnight under $N_2$, the mixture concentrated in vacuo, then loaded onto a short silica column. Flash chromatography using a mixture of hexane (90%) and $Et_2O$ (10%) as eluent, gave 4,8-cyclododecadiene carboxaldehyde (QRM 2815) as a colourless oil (14.0 g).

b) Synthesis of 1-(4,8-Cyclododecadienyl)-2-methyl-1-propanone (QRM 2885)

Figure 1:
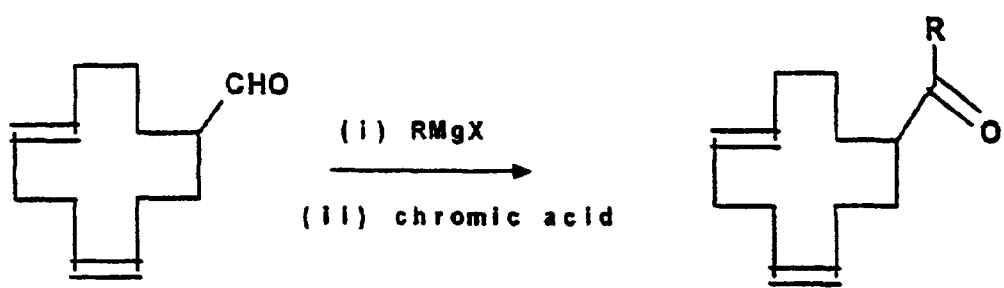
FIG. 1 illustrates the production of the ketone from 4,8-cyclododecadiene-1-carbaldehyde.

The reaction is shown in FIG. 1. where R is iso-propyl.

4,8-Cyclododecadiene carboxaldehyde (QRM 2185) [14.0 g; 0.072 mol] was dissolved in THF (50 ml), and isopropylmagnesium chloride [36 ml; 2.0 M in $Et_2O$, 0.072 mol] was added dropwise with stirring under $N_2$. The reaction mixture was stirred for 30 minutes, most solvent was removed in vacuo, and the residue quenched with saturated ammonium chloride solution, then partitioned ($Et_2O$/$H_2O$). The organic layer was separated, washed and dried over $MgSO_4$. The solvent was removed in vacuo, and the residue was chromatographed [silica: $Et_2O$ 50%, hexane 50%] to give 1-(4,8-cyclododecadienyl)-2-methyl-1-propanol (11.1 g, 65%) as a colourless oil.

This material was dissolved in $Et_2O$ (150 ml), and chromic acid [from sodium dichromate (10 g), $H_2SO_4$ (10 ml), and $H_2O$ (50 ml)] added dropwise, with stirring. The reaction mixture was partitioned between $Et_2O$ and H2O, and the organic layer was separated, washed and dried.

Chromatography [silica; $Et_2O$ 10%, hexane 90%] gave a colourless oil which was short-path distilled, bp 125° C. at 3 mbar, 6.3 g (58%).

Glc [SE54; 100–250° C. at 4° C./min] 22.512 min (7%) M+234, 23.118 min (89%) M+234.

Figure 3:
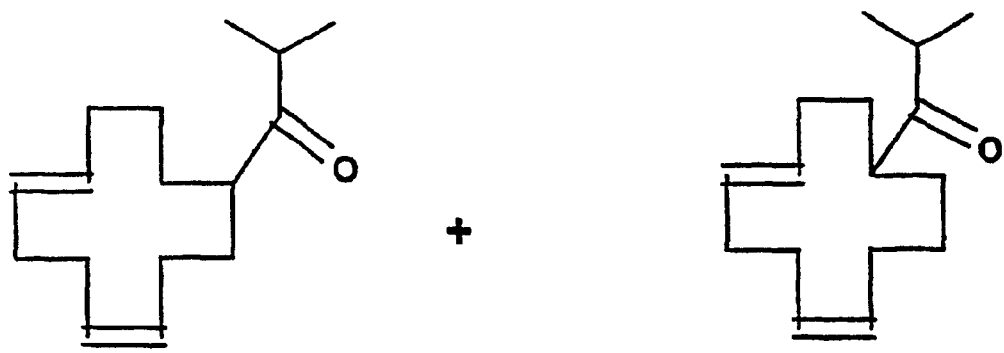
FIG. 3 shows the two geometrical isomers of 1-(4,8-cyclododecadienyl)-2-methyl-1-propanone (QRM 2885).

The material produced was an isomeric mixture of (Z,E)-1-(4,8-cyclododecadienyl)-2-methyl-1-propanone (89%), and (E,Z)-1-(4,8-cyclododecadienyl)-2-methyl-1-propanone (7%), as shown in FIG. 3.

As noted above, other ketones in accordance with the invention may be produced from the aldehyde QRM 2815 by reaction with a range of Grignard reagents, followed by oxidation, as illustrated generally in FIG. 1.

EXAMPLE 2

Experiments were carried out to test the stability and substantivity of 1-(4,8-cyclododecadienyl)-2-methyl-1-propanone (QRM 2885) in the form of the isomeric mixture produced as described in Example 1.

a) In-product Stability Testing

The performance of QRM 2885 was compared with that of two known fragrance materials, Cyclisone (Cyclisone is a Trade Mark) from Quest International and Iso E Super (Iso E Super is a Trade Mark) from Acedesa.

All three fragrance materials were dosed individually into a selected range of product bases (listed below) and were subjected to accelerated storage. Assessment for olfactory and colour stability was carried out by a panel of perfumers and synthetic chemists after 4 and 12 weeks storage.

The product bases and fragrance doses in % W/W employed for this study were:

Alcohol (1%)

Soap Base No. 2 (0.5%)

Shampoo (0.3%)

Citric Acid Toilet Cleaner (0.5%)

Fabric Conditioner—Hamburg Ester Quaternary (HEQ) (0.3%)

Heavy duty laundry liquid (HDLL) (Marilyn) (0.3%)

Antiperspirant (Aluminium chlorohydrate (ACH) Roll-On) (0.3%)

Tetraacetylethylenediamine (TAED)/Perborate Laundry Powder (0.3%)

Laundry Powder Detergent (Surf) (0.5%)

In addition, samples of QRM 2885 in HEQ fabric conditioner and soap base No. 2 were assessed for their chemical stability after 12 weeks accelerated storage at 37° C. Extraction was performed by standard laboratory methods. HEQ samples were stored in 15 ml glass bottles, and soaps were stored as small bars in waxpaper packaging.

The conclusions were as follows:

1. QRM 2885 was assessed as having a "good" or "good/moderate" performance in alcohol, soap, shampoo, fabric conditioner, antiperspirant and Surf laundry powder after 12 weeks storage at 37° C. (37° C./70% RH for laundry powder). It also recorded a "moderate" performance in TAED/perborate laundry powder.

2. QRM 2885 was assessed as having a better performance/stability than both Cyclisone and Iso E Super in soap, fabric conditioner, TAED/perborate laundry powder and Surf laundry powder.

3. In the other product bases (i. e. alcohol, shampoo and antiperspirant) the performance of QRM 2885 was considered to be equivalent or better than either Cyclisone or Iso E Super.

4. QRM 2885, Cyclisone and Iso E Super all exhibited "poor" stability/performance in citric acid toilet cleaner and HDLL.

5. Chemical stability of QRM 2885, after 12 weeks storage at 37° C.

| | % remaining |
| --- | --- |
| Fabric conditioner (HEQ) | 66% |
| Soap base No. 2 | 100% | b) Fibre Substantivity Testing

The same three fragrance materials were assessed for their fibre substantivity on terry towelling from the HEQ fabric conditioner base.

All fragrance ingredients were dosed at 0.25% wt/wt into regular strength HEQ fabric conditioner. The fabric conditioner was then dosed at 3 g/l of water into the tergotometer, mixed and two pieces of terry towelling added and agitated at 100 rpm for 10 minutes.

The cloths were then assessed line dried and damp by 5 creative perfumers.

The results from this fibre substantivity assessment showed QRM 2885 has good fibre substantivity on both damp and dry terry towelling, with QRM 2885 out performing the standards Cyclisone and Iso E Super in three out of the five assessments.

EXAMPLE 3

A rhodium catalyst, Rh-42, [Carbonylhydridotris (triphenylphosphine)rhodium(I)] was dissolved in cis,trans,trans-cyclododeca-1,5,9-triene at a concentration of 0.5 molar per cent and the resulting solution was stirred rapidly under an atmosphere of 1:1 $CO/H_2$ by volume at a pressure of 1 MPa for 45 hrs. The temperature was maintained at 70 to 80° C. and the reaction was followed by glc. The crude reaction mixture was passed through a wiped film evaporator to remove the rhodium catalyst and 4,8-cyclododecadiene-1-carbaldehyde was separated by distillation. The yield of 4,8-cyclododecadiene-1-carbaldehyde was 55%. This aldehyde was then converted to 1-(4,8-cyclododecadienyl)-2-methyl-1-propanone by reaction with isopropylmagnesium chloride as described in part (b) of Example 1. The material produced contained about 91% of an isomeric mixture of (Z,E)-1-(4,8-cyclododecadienyl)-2-methyl-1-propanone and (E,Z)-1-(4,8-cyclododecadienyl)-2-methyl-1-propanone, these two isomers being present in approximately equal amounts.

What is claimed is:

1. A 4,8-cyclododecadienyl ketone, having the formula shown below

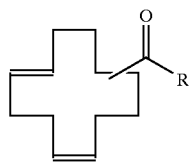

(I)

in which R is an alkyl group having up to 5 carbon atoms.

2. A ketone according to claim 1, wherein R is iso-propyl.

3. A ketone according to claim 2, comprising a mixture of the geometrical isomers (Z,E)-4,8-cyclododecadienyl-2-methyl-1-propanone and (E,Z)-4,8-cyclododecadienyl-2-methyl-1-propanone.

4. A method of making the compound according to any one of claims 1 to 3, comprising reacting 4,8-cyclododecadiene-1-carbaldehyde with a Grignard reagent, followed by oxidation.

5. A method according to claim 4 wherein the 4,8-cyclododecadiene-1-carbaldehyde is prepared by reaction of 1,5,9-cyclododecatriene with a peroxy acid to form 1,5,9-cyclododecatriene monoepoxide followed by catalysed isomerisation.

6. A method according to claim 4 wherein the 4,8-cyclododecadiene-1-carbaldehyde is prepared by hydroformylation of 1,5,9-cyclododecatriene with carbon monoxide and hydrogen.

7. A perfume comprising the ketone of claim 1 in an olfactively effective amount.

8. A perfume according to claim 7, wherein the ketone is present in an amount of at least 0.01% by weight.

9. A perfume according to claim 8, wherein the ketone is present in an amount in the range 0.1 to 80% by weight.

10. A perfumed product comprising a ketone according to claim 1 or a perfume according to claim 7.

* * * * *